United States Patent
Lacroix-Desmazes et al.

(10) Patent No.: US 7,741,524 B2
(45) Date of Patent: Jun. 22, 2010

(54) IODINATED ORGANIC SUBSTANCES OF LOW MOLECULAR MASS AND PROCESS FOR PREPARING THEM

(75) Inventors: Patrick Lacroix-Desmazes, Montpellier (FR); Romain Severac, Grabels (FR); Bernard Boutevin, Montpellier (FR); Vincent Bodart, Tavaux (FR); Vincent Kurowski, Estaimbourg (BE)

(73) Assignee: Solvay (Societe Anonyme), Brussels (BE)

( * ) Notice: Subject to any disclaimer, the term of this patent is extended or adjusted under 35 U.S.C. 154(b) by 702 days.

(21) Appl. No.: 10/553,993

(22) PCT Filed: Apr. 22, 2004

(86) PCT No.: PCT/EP2004/050591

§ 371 (c)(1),
(2), (4) Date: Aug. 3, 2006

(87) PCT Pub. No.: WO2004/094356

PCT Pub. Date: Nov. 4, 2004

(65) Prior Publication Data

US 2007/0066781 A1   Mar. 22, 2007

Related U.S. Application Data

(60) Provisional application No. 60/487,258, filed on Jul. 16, 2003.

(30) Foreign Application Priority Data

Apr. 22, 2003 (BE) ................... 2003/0255
Aug. 1, 2003 (FR) ................... 03 09561

(51) Int. Cl.
C07C 41/06 (2006.01)
C07C 43/12 (2006.01)
C07C 69/96 (2006.01)
C07C 305/00 (2006.01)
C07C 309/65 (2006.01)

(52) U.S. Cl. ................... 570/246
(58) Field of Classification Search ............ None
See application file for complete search history.

(56) References Cited

U.S. PATENT DOCUMENTS

| | | | |
|---|---|---|---|
| 5,055,713 A * | 10/1991 | Watanabe et al. | 326/27 |
| 5,144,067 A | 9/1992 | Zoeller et al. | |
| 5,430,208 A * | 7/1995 | Bak et al. | 570/250 |
| 5,455,319 A | 10/1995 | Bak et al. | |
| 6,982,106 B2 | 1/2006 | Bodart et al. | |
| 7,078,473 B2 * | 7/2006 | Lacroix-Desmazes et al. | 526/343 |
| 2004/0097625 A1 | 5/2004 | Bodart et al. | |
| 2004/0198702 A1 | 10/2004 | Petrova et al. | |
| 2005/0171312 A1 | 8/2005 | Lacroix-Desmazes et al. | |
| 2006/0205906 A1 | 9/2006 | Lacroix-Desmazes et al. | |

FOREIGN PATENT DOCUMENTS

EP   0 510 281   10/1992

OTHER PUBLICATIONS

March et al. "Advanced organic chemistry", Fifth edition, 2001, p. 977.*
Chambers et al. Journal of fluorine chemistry, 1995, 73, 87-94.*
Perret et al. Helv. Chem. Acta 1945, 28, 558-575; translation.*
U.S. Appl. No. 11/687,461, filed Mar. 16, 2007, Lacroix_Desmazes, et al.
Perret et al. "73. Contribution a l'etude de l'action oxydante du peroxyde de benzoyle, en presence d'iode, sur quelques carbures d'hydrogene non satures", Helv. Chim. Acta., vol. 28, pp. 558-575 1945.
Heasley et al. "Addition of tert-Butyl Hypoiodite to Selected Olefins", J. Org. Chem., vol. 53, pp. 198-201 1988.
Cambie et al. "Thallium(I) Carboxylates: A New Class of Reagents for the Formation of alpha-Iodocarboxylates", J.C.S. Chem. Comm., pp. 359-360 1973.
Jo et al. "New AB or ABA type block copolymers: atom transfer radical polymerization (ATRP) of methyl methacrylate using iodine-terminated PVDFs as (macro)initiators", Polymer Bulletin, vol. 44, pp. 1-8 2000.

(Continued)

*Primary Examiner*—Daniel M Sullivan
*Assistant Examiner*—Yevegeny Valenrod
(74) *Attorney, Agent, or Firm*—Oblon, Spivak, McClelland, Maier & Neustadt, L.L.P.

(57) ABSTRACT

Process for preparing one or more iodinated organic substances having a molecular mass of less than 2000 (substances (S)) using (A) at least one free-radical-generating substance chosen from peroxides, diazo compounds, dialkyldiphenylalkanes, substances derived from tetraphenylethane, boranes and iniferter substances comprising at least one thiuram disulphide group, (B) an ethylenically unsaturated substance capable of adding a free radical to its ethylenic double bond, (C) molecular iodine, which comprises the steps according to which at least a fraction of (A), at least a fraction of (B) and at least a fraction of (C) are introduced into a reactor, and then the contents of the reactor are caused to react, while introducing therein the possible remainder of (A), the possible remainder of (B) and the possible remainder of (C), until a moment is reached when the content of the reactor is a mixture comprising one or more substances (S). Iodinated organic substances for whose preparation the abovementioned process is particularly well suited.

19 Claims, 1 Drawing Sheet

OTHER PUBLICATIONS

Brace. "Syntheses with perfluoroalkyl iodides. A review Part III. Addition of RFI to norbornene esters, acids and anhydrides, alkenoic acids and esters, alkenylsuccinic anhydrides or diesters, and to vinyl monomers; lactonization and other reactions of adducts; hydroperfluoroalkylation by RFI; synthesis and reactions of I(CF2)nI homologues (n=1-3); perfluoroalkylation of arenes by RFI or [RFCO2]2; RFI in the synthesis of RFSR and segmented RF(CH2)nSH; and useful derivatives therefrom", Journal of Fluorine Chemistry, vol. 108, pp. 147-175 2001.

Chambers et al. "A new telogen for telechelic oligomers of chlorotrifluoroethylene", Journal of Fluorine Chemistry, vol. 73, pp. 87-94 1995.

\* cited by examiner

Figure 1

IODINATED ORGANIC SUBSTANCES OF LOW MOLECULAR MASS AND PROCESS FOR PREPARING THEM

This application is a 371 of PCT/EP04/50591 filed Apr. 22, 2004, and claims benefit of U.S. provisional application Ser. No. 60/487,258, filed Jul. 16, 2003.

The present invention relates to a process for preparing iodinated organic substances of low molecular mass, iodinated organic substances of low molecular mass, and a process for preparing a polymer involving these iodinated organic substances of low molecular mass.

U.S. Pat. No. 5,144,067 describes a process for the coproduction of an alkyl iodide on the one hand, and of a mono-α-iodocarboxylic acid and/or anhydride on the other hand, according to which a mixture of an iodinated compound, for example molecular iodine, a carboxylic anhydride, such as acetic anhydride, and a peroxide, such as hydrogen peroxide, is caused to react at a high temperature.

U.S. Pat. No. 5,430,208 describes a process for synthesizing 1-chloro-1-iodoethane according to which a hydriodic acid is reacted with vinyl chloride in the presence of an iodine-containing catalyst which is organic (such as 1,2-diiodoethane) or inorganic (such as potassium iodide or molecular iodine).

Heasley et al., J. Org. Chem. 1988, pp. 198-201 have synthesized various iodinated organic substances by reacting tort-butyl hypoiodide with various ethylenically unsaturated substances, in the presence of $BF_3$ or under the action of ultraviolet radiation. In particular, they thus synthesized the substance of formula $(CH_3)_3$—C—O—$CH_2$—CHΦI, where Φ denotes a phenyl group.

Cambie et al., J. Chem. Soc., Chem. Comm., 1973, vol. 11, pp. 359-360 have also synthesized the substance $(CH_3)_3$—C—O—$CH_2$—CHΦI by reacting sterene, molecular iodine and thallium(I) acetate.

The processes for synthesizing iodinated organic substances of low molecular mass of the prior art are complicated processes. They additionally require the use of raw materials which are expensive and/or dangerous to handle. The iodinated organic substances of low molecular mass thus produced are themselves very expensive.

It is also known that several iodinated organic substances of low molecular mass can be used as initiators for controlled free-radical polymerization (polymerizations of the "ITP" type).

However, the "best" choice in terms of efficiency of initiation of the polymerization and the properties of the polymers thus produced often depends on the actual nature of the monomers, hence they need to have available a fairly broad range of iodinated organic initiators if it is desired to polymerize monomers of a different chemical nature, all under optimum conditions.

The subject of the present invention is a process of preparation which makes it possible to both have all the advantages of the prior art processes and to avoid all the disadvantages thereof.

To this effect, the invention relates to a process for preparing one or more iodinated organic substances having a molecular mass of less than 2000 (substances (S)) using:
(A) at least one free-radical-generating substance chosen from peroxides, diazo compounds, dialkyldiphenylalkanes, substances derived from tetraphenylethane, boranes and iniferter substances comprising at least one thiuram disulphide group,
(B) at least one organic substance containing at least one ethylenic double bond, capable of adding a free radical to its ethylenic double bond,
(C) molecular iodine, which comprises the steps according to which:
(1) at least a fraction of (A), at least a fraction of (B) and at least a fraction of (C) are introduced into a reactor, and then
(2) the contents of the reactor are caused to react, while introducing therein the possible remainder of (A), the possible remainder of (B) and the possible remainder of (C), until a moment is reached when the content of the reactor is a mixture comprising one or more substances (S) [mixture (M)].

In addition to the substance(s) (S), one or more iodinated organic substances other than the substance(s) (S) may be optionally prepared by the process according to the invention [substances (S')].

The weight of the iodinated organic substance(s) (S') expressed relative to the weight of the substance(s) (S) is preferably less than 1, in a particularly preferred manner less than 0.2 and in a most particularly preferred manner less than 0.05.

The substance(s) (S) have a molecular mass preferably of less than 1000, in a particularly preferred manner of less than 500 and in a most particularly preferred manner of less than 250.

The substance(s) (S) have a number-average molecular mass advantageously of less than 500, preferably of less than 250.

The expression peroxides is understood to mean both organic peroxides and inorganic peroxides.

A first family of substances among which the free-radical-generating substance is preferably chosen is that of organic peroxides.

By way of examples of organic peroxides, there may be mentioned:
dialkyl peroxides such as dicumyl peroxide, tert-butyl and cumyl peroxide and di-tert-butyl peroxide;
diacyl peroxides such as diisononanoyl peroxide, dioctanoyl peroxide, didecanoyl peroxide, dilauroyl peroxide, di(2-methylbenzoyl) peroxide, dibenzoyl peroxide and di(4-chlorobenzoyl) peroxide;
acetyl cyclohexane sulphonyl peroxide;
dialkyl peroxydicarbonates such as diethyl peroxydicarbonate, diisopropyl peroxydicarbonate, di(sec-butyl) peroxydicarbonate, dimyristyl peroxydicarbonate, dicetyl peroxydicarbonate, di(2-ethylhexyl) peroxydicarbonate and di(4-tert-butylcyclohexyl) peroxydicarbonate;
dialkyl percarbonates such as tert-amylperoxy-2-ethylhexyl carbonate and tert-butylperoxyisopropyl carbonate;
peresters such as cumyl perneodecanoate, tert-amyl perneodecanoate, tert-butyl perpivalate, tert-butyl per(2-ethylhexanoate), tert-butyl periso-butyrate, tert-butyl perisononanoate, 2,5-dimethylhexane 2,5-diperbenzoate, tert-butyl perbenzoate;
perketals such as 1,1-bis(tert-butylbutylperoxy)cyclohexane and 2,2-bis(tert-butylperoxy)butane;
ketone peroxides such as methyl ethyl ketone peroxide, cyclohexanone peroxide and acetyl acetone peroxide;
organic hydroperoxides such as cumene hydroperoxide, tert-butyl hydroperoxide and pinane hydroperoxide.

The organic peroxides are preferably chosen from dialkyl peroxides, diacyl peroxides, dialkyl peroxydicarbonates and peresters. They are chosen in a particularly preferred manner from dialkyl peroxides and dialkyl peroxydicarbonates, and in a most particularly preferred manner from dialkyl peroxides in which each of the alkyl chains comprises at most 4 carbon atoms and dialkyl peroxydicarbonates in which each of the alkyl chains comprises at most 4 carbon atoms. Di-tert-butyl peroxide and diethyl peroxydicarbonate gave excellent results.

A second family of substances, among which the free-radical-generating substance is preferably chosen is that of the inorganic peroxides.

By way of examples of inorganic peroxides, there may be mentioned:
  hydrogen peroxide;
  persulphates such as ammonium persulphate, sodium persulphate and potassium persulphate;
  perborates.

The inorganic peroxides are preferably persulphates. Ammonium persulphate gave excellent results.

A third family of substances among which the free-radical-generating substance is preferably chosen is that of diazo compounds.

By way of examples of diazo compounds, there may be mentioned azobis(isobutyronitrile), azobis(2,4-dimethylvaleronitrile), azoamidines and azomidinium salts.

The diazo compounds preferably carry one or more nitrile groups. Azobis(isobutyronitrile) gave excellent results.

By way of examples of dialkyldiphenylalkanes, there may be mentioned 3,4-dimethyl-3,4-diphenylhexane and 2,3-dimethyl-2,3-diphenylbutane.

By way of examples of substances derived from tetraphenylethane, there may be mentioned N≡C—C$\Phi_2$-C$\Phi_2$-C≡N, $\theta$O—C$\Phi_2$-C$\Phi_2$—O$\theta$, $\theta_3$Si—C$\Phi_2$-C$\Phi_2$—Si$\theta_3$, ($\theta$O)$_3$Si—C$\Phi_2$-C$\Phi_2$-Si(O$\theta$)$_3$ and $\Phi$O—C$\Phi_2$-C$\Phi_2$-O$\Phi$; in the substances exemplified above; $\Phi$ is a phenyl group and $\theta$ is a $C_1$-$C_{20}$ alkyl group.

By way of examples of boranes, there may be mentioned trialkylboranes (B(OO$\theta$)$_3$) such as trimethylborane and triphenylborane (B(OO$\Phi$)$_3$), $\theta$ and $\Phi$ as defined above.

By way of examples of iniferter substances comprising at least one thiuram disulphide group, there may be mentioned $\theta_2$N—(S═)C—S—S—C(═S)—N$\theta_2$, the $\theta$ symbols, which are equal or different, being as defined above.

The organic substance containing at least one ethylenic double bond capable of adding a free radical to its ethylenic double bond advantageously corresponds to the formula C$\Psi_2$═C$\Psi\Xi$ where
  the $\Psi$ symbols represent, independently of each other and of $\Xi$, (i) a hydrogen atom, (ii) a halogen atom other than an iodine atom, or (iii) a linear or branched $C_1$-$C_{20}$ alkyl group;
  $\Xi$ resents (i) a halogen atom other than an iodine atom, (ii) a phenyl group optionally substituted with one or more atoms chosen from halogen atoms other than the iodine atom and $C_1$-$C_8$ alkyl groups, (iii) a group —O—C(═O)—, (iv) a nitrile group, (v) a group —C(═O)—O-$\Omega$, or (vi) a group —C(═O)—N$\Omega_2$;
  $\Omega$ represents (i) a hydrogen atom, or (ii) a saturated or ethylenically unsaturated or aromatic $C_1$-$C_{20}$ hydrocarbon group.

A first family of preferred substances corresponding to the formula C$\Psi_2$═C$\Psi\Xi$ is that where $\Xi$ represents a halogen atom other than an iodine atom ([family (F1)].

The substances of the family (F1) preferably have at most 3 carbon atoms. In a particularly preferred manner, they are chosen from vinyl chloride, vinylidene chloride, trichlorethylene, chlorotrifluoroethylene, vinyl fluoride, vinylidene fluoride, trifluoroethylene, tetrafluoroethylene and hexafluoropropylene. In a most particularly preferred manner they are chosen from vinyl chloride, vinylidene chloride and hexafluoropropylene.

A second family of preferred substances corresponding to the formula C$\Psi_2$═C$\Psi\Xi$ is that where $\Xi$ represents a phenyl group, optionally substituted with one or more atoms chosen from halogen atoms other than the iodine atom and $C_1$-$C_8$ alkyl groups [family (F2)].

The substances of the family (F2) preferably correspond to the formula CH$_2$═CH$\Xi$, $\Xi$ as defined in the preceding paragraph. Among all the substances of the family (F2), styrene gave excellent results.

A third family of preferred substances corresponding to the formula C$\Psi_2$═C$\Psi\Xi$ is that where $\Xi$ represents a group —O—C(═O)-$\Omega$, $\Omega$ as defined above [family (F3)].

The substances of the family (F3) preferably correspond to the formula CH$_2$═CH$\Xi$, $\Xi$ as defined in the preceding paragraph. Among all the substances of the family (F3), vinyl acetate gave excellent results.

A fourth family of preferred substances corresponding to the formula C$\Psi_2$═C$\Psi\Xi$ is that where $\Xi$ represents a group chosen from the nitrile group and from the groups —C(═O)—O-$\Omega$ and —C(═O)—N$\Omega_2$, $\Omega$ as defined above [family (F4)].

The substances of the family (F4) preferably correspond either to the formula CH$_2$═CH$\Xi$, or to the formula CH$_2$═C(CH$_3$)$\Xi$, or else to the formula CH$_2$═CF$\Xi$, $\Xi$ as defined in the preceding paragraph. In a particularly preferred manner, they correspond to the formula CH$_2$═CH—C(═O)—O-$\Omega$ or to the formula (CH$_2$═C(CH$_3$)—C(═O)—O-$\Omega$, $\Omega$ as defined above. In a more particularly preferred manner, they are chosen from acrylic acid, methyl acrylate, ethyl acrylate, n-butyl acrylate, 2-ethylhexyl acrylate, methacrylic acid, methyl methacrylate and n-butyl methacrylate. Among all the substances of the family (F4), methyl acrylate gave excellent results.

As examples of organic substances containing at least one ethylenic double bond and capable of adding a free radical to their ethylenic double bond other than the abovementioned substances, there may be mentioned ethylene, propylene and butadiene.

When the process according to the invention uses several organic substances containing at least one ethylenic double bond, which are capable of adding a free radical to their ethylenic double bond, advantageously at least one of them is chosen from the substances of the family (F1) and at least another is chosen from the substances of the families (F3) and (F4). Preferably, at least one of them is chosen from vinyl chloride, vinylidene chloride and vinylidene fluoride and at least another is chosen from vinyl acetate, methyl acrylate and n butyl acrylate. In a particularly preferred manner, one of them is vinylidene chloride and another is methyl acrylate.

The temperature at which the contents of the reactor are caused to react is advantageously from −50° C. to 300° C., preferably from 0 to 150° C.

Preferably, the whole of (A), (B) and (C) is introduced into the reactor in step (1).

According to a first preferred variant of the process according to the invention [variant (1)], the contents of the reactor are caused to react until the quantity of (B) consumed by the reaction no longer changes.

According to the variant (1), the number of moles of (C) expressed relative to the number of moles of (A) is advantageously greater than or equal to 90%, preferably greater than or equal to 100% and in a particularly preferred manner greater than or equal to 105%. In addition, the number of moles of (C) expressed relative to the number of moles of (A) is advantageously less than 200% and preferably less than 150%.

According to the variant (1), the number of moles of (C) expressed relative to the number of moles of (B) is usually more than 0.5%. It may be greater than 5%, or even greater than 50%, and may even sometimes exceed 100%, without the good operation of the process according to the invention being affected. In addition, the number of moles of (C) expressed relative to the number of moles of (B) is advantageously less than 200% and preferably less than 150%.

According to a second preferred variant of the process according to the invention [variant (2)], the process additionally comprises a step (3), following step (2), according to which the reaction in progress is stopped, for example by suddenly cooling the contents of the reactor.

According to the variant (2), the moment when the reaction in progress is stopped is advantageously that when the colour of the contents of the reactor changes from a dark colour to a light colour.

According to the variant (2), the number of moles of (C) expressed relative to the number of moles of (A) is advantageously less than 100% and preferably less than 90%. In addition, the number of moles of (C) expressed relative to the number of moles of (A) is advantageously greater than or equal to 20%.

According to the variant (2), the number of moles of (C) expressed relative to the number of moles (B) is usually less than 100%. It may be less than 50%, or even less than 5%, and may even sometimes be less than 1%, without the good operation of the process according to the invention being affected. In addition, the number of moles of (C) expressed relative to the number of moles of (B) is advantageously greater than or equal to 0.01% and preferably greater than 0.1%.

The process according to the invention advantageously comprises in addition one step, following step (2) and, furthermore, following step (3), when the process comprises the said step (3), according to which at least one substance (S) of the mixture (M) and possible other substances (S) contained in the mixture (M) are isolated.

The subject of the present invention is also iodinated organic substances for the preparation of which the process which is the subject of the invention is particularly well suited, and which all have the advantages of the iodinated organic substances of the prior art without exhibiting the disadvantages thereof.

To this effect, the invention relates to a mixture comprising at least 2 iodinated organic substances having a molecular mass of less than 2000, corresponding respectively to the general formulae R-$G_x$($CX_2$—CXY—)$_n$—I and R-$G_x$($CX_2$—CXY—)$_{n+1}$—I, where:

R represents (i) a hydrogen atom, (ii) an atom of an alkali metal, (iii) a linear or branched $C_1$-$C_{20}$ alkyl group optionally substituted with one or more groups chosen from phenyl, carboxyl, hydroxyl, nitrile, amine or amidine groups, (iv) a $C_3$-$C_8$ cycloalkyl group optionally substituted with one or more groups chosen from $C_1$-$C_8$ alkyl groups and the nitrile group, or (v) a phenyl group, optionally substituted with one or more groups chosen from the $C_1$-$C_4$ alkyl groups and halogen atoms other than the iodine atom;

x represents an integer equal to 0 or 1;

G represents —O—, —O(=O)—O—, —C(=O)—O— or —O—S(=O)$_p$—O—;

if G is a group —C(=O)—O—, then its fragment C(=O) is linked to R and its fragment O linked to a group $CX_2$;

p represents an integer equal to 1 or 2;

n represents an integer equal to 1 to 8;

the groups X represent, independently of each other and of Y, (i) a hydrogen atom, (ii) a halogen atom other than an iodine atom, or (iii) a linear or branched $C_1$-$C_{20}$ alkyl group;

Y represents (i) a halogen atom other than an iodine atom, (ii) a phenyl group optionally substituted with one or more atoms chosen from halogen atoms other than the iodine atom and $C_1$-$C_8$ alkyl groups, (iii) a group —O—C(=O)—Z, (iv) a nitrile group, (v) a group —C(=O)—O—Z, or (vi) a group —C(=O)—$NZ_2$;

Z represents (i) a hydrogen atom, or (ii) a saturated or ethylenically unsaturated or aromatic $C_1$-$C_{20}$ hydrocarbon group;

R, G, x, $CX_2$—CXY and n are identical for the 2 substances which are the subject of the invention;

I is an iodine atom

[substances (S2)].

The substances (S2) have a number-average molecular mass advantageously of less than 500 and preferably of less than 250.

Each of the substances (S2) has a molecular mass preferably of less than 1000, in a particularly preferred manner of less than 500 and in a most particularly preferred manner of less than 250.

By way of examples of alkali metal atoms capable of constituting the group R, sodium and potassium may be mentioned.

By way of examples of unsubstituted alkyl groups capable of constituting the group R, there may be mentioned methyl, ethyl, isopropyl, sec-butyl, tert-butyl, tert-amyl, n-heptyl, (1-ethyl)pentyl, (2-ethyl)hexyl, (2-methyl)-(4,4-dimethyl)pentyl, n-nonyl, n-undecyl, myristyl and cetyl groups.

By way of examples of substituted alkyl groups capable of constituting the group R, there may be mentioned cumyl, —C(C≡N)—$(CH_3)_2$, (2-phenyl)propyl and (2-phenyl)butyl groups.

By way of examples of substituted or unsubstituted cycloalkyl groups capable of constituting the group R, there may be mentioned cyclohexyl and pinyl groups.

By way of examples of substituted phenyl groups capable of constituting the group R, there may be mentioned (2-methyl)phenyl and (4-chlorophenyl) groups.

As regards the substances (S2), n is usually less than 7, and often less than 5.

As regards the substances (S2), G is preferably chosen from the groups —O—C(=O)—O—, —O—, —O—S(=O)—O— and —O—S(=O)—O—. Two groups G are particularly preferred: one is the group —O—C(=O)—O—; the other is the group —O—S(=O)$_2$—O—.

The mixture according to the invention is advantageously free of iodinated organic substances having a molecular mass of greater than or equal to 2000; it is preferably free of iodinated organic substances having a molecular mass of greater than or equal to 1000.

The expression "free of ( . . . )" is understood to mean "not containing a detectable quantity of ( . . . ) by any size exclusion chromatography technique known to a person skilled in the art".

A first family of preferred substances (S2) is that of the substances (S2) where Y represents a halogen atom other than an iodine atom [family (F'1)].

The groups (—$CX_2$—CXY—) of the substances (S2) of the family (F'1) advantageously have at most 3 carbon atoms. They are preferably chosen from the groups (—$CH_2$—CHCl—), (—$CH_2$—$CCl_2$—), (—$CCl_2$—CHCl—), (—$CF_2$—CFCl—), (—$CH_2$—CHF—), (—$CH_2$—$CF_2$—), (—$CF_2$—CHF—), (—$CF_2$—$CF_2$—) and (—$CF_2$—CF($CF_3$)—). In a particularly preferred manner they are chosen from the groups (—$CH_2$—CHCl—), (—$CH_2$—$CCl_2$—), (—$CH_2$—$CF_2$—) and (—$CF_2$—CF($CF_3$)—).

A second family of preferred substances (S2) is that of the substances (S2) where Y represents a phenyl group, optionally substituted with one or more atoms chosen from halogen atoms other than the iodine atom and $C_1$-$C_8$ alkyl groups [family (F'2)].

The groups (—$CX_2$—CXY—) of the substances (S2) of the family (F'2) advantageously correspond to the formula (—$CH_2$—CHY—), Y as defined in the preceding paragraph. Among all these groups, the group (—$CH_2$—CHΦ-), where Φ denotes a phenyl group, is preferred.

A third family of preferred substances (S2) is that of the substances (S2) where Y represents a group —O—C(=O)—Z, Z as defined above [family (F'3)].

The groups (—$CX_2$—CXY—) of the substances (S2) of the family (F'3) advantageously correspond to the formula (—$CH_2$—CHY—), Y as defined in the preceding paragraph. Among all these groups, the acetyl group is preferred.

A fourth family of preferred substances (S2) is that of the substances (S2) where Y represents a group chosen from the nitrile group, the groups —C(=O)—O—Z and —C(=O)—$NZ_2$, Z as defined above [family (F'4)].

The groups (—$CX_2$—CXY—) of the substances (S2) of the family (F'4) advantageously correspond either to the formula (—$CH_2$—CHY—), or to the formula (—$CH_2$—C($CH_3$)Y—), or else to the formula (—$CH_2$—CFY—), Y as defined in the preceding paragraph. They preferably correspond to the formula (—$CH_2$—CH(C(=O)OZ—) or to the formula (—$CH_2$—C($CH_3$)(C(=O)OZ)—), Z as defined above. In a particularly preferred manner, they are chosen from the groups formed by the opening of the ethylenic double bond of one of the following substances: acrylic acid, methyl acrylate, ethyl acrylate, n-butyl acrylate, 2-ethylhexyl acrylate, methacrylic acid, methyl methacrylate and n-butyl methacrylate. Among all these groups, the group (—$CH_2$—CH(C(=O)O($CH_3$))—), that is to say the group formed by the opening of the ethylenic double bond of methyl acrylate, is most particularly preferred.

The invention also relates to an iodinated organic substance having a molecular mass of less than 2000, corresponding to the general formula (I)

with R, G, X, Y and I as defined above for the substances (S2) and where q represents an integer greater than 1 and less than 10.

The substance corresponding to the formula (I) has a molecular mass preferably of less than 1000, in a particularly preferred manner of less than 500 and in a most particularly preferred manner of less than 250.

q is usually less than 7, and often less than 5.

As regards the substance corresponding to the formula (I), G is preferably chosen from the groups C(=O)—C(=O)—O—, —O—, —O—S(=O)—O— and —O—S(=O)$_2$—O—. Two groups G are particularly preferred: one is the group —O—C(=O)—O—; the other is the group —O—S(=O)$_2$—O—.

A first family of preferred substances corresponding to the formula (I) is that where Y represents a halogen atom other than an iodine atom [family (F'''1)]. The groups (—$CX_2$—CXY—) of the substances of the family (F'''1) satisfy the same characteristics and conditions preferably as the groups (—$CX_2$—CXY—) of the substances (S2) of the family (F'1).

A second family of preferred substances corresponding to the formula (I) is that where Y represents a phenyl group, optionally substituted with one or more atoms chosen from the halogen atoms other than the iodine atom and $C_1$-$C_8$ alkyl groups [family (F'''2)].

The groups (—$CX_2$—CXY—) of the substances of the family (F'''2) satisfy the same characteristics and conditions preferably as the groups (—$CX_2$—CXY—) of the substances (S2) of the family (F'2).

A third family of preferred substances corresponding to the formula (I) is that where Y represents a group —O—C(=O)—Z, Z as defined above [family (F'''3)].

The groups (—$CX_2$—CXY—) of the substances of the family (F'''3) satisfy the same characteristics and conditions preferably as the groups (—$CX_2$—CXY—) of the substances (S2) of the family (F'3).

A fourth family of preferred substances corresponding to the formula (I) is that where Y represents a group chosen from the nitrile group, the groups —C(=O)—O—Z and —C(=O)—$NZ_2$, Z as defined above [family (F'''4)].

The groups (—$CX_2$—CXY—) of the substances of the family (F'''4) satisfy the same characteristics and conditions preferably as the groups (—$CX_2$—CXY—) of the substances (S2) of the family (F'4).

The invention also relates to an iodinated organic substance having a molecular mass of less than 2000, corresponding to the general formula (II)

with R, X, Y and I as defined above for the substances (S2).

The substance corresponding to the formula (II) has a molecular mass preferably of less than 1000, in a particularly preferred manner of less than 500 and in a most particularly preferred manner of less than 250.

A first family of preferred substances corresponding to the formula (II) is that where Y represents a halogen atom other than an iodine atom [family (F'''1)].

The groups (—$CX_2$—CXY—) of the substances of the family (F'''1) satisfy the same characteristics and conditions preferably as the groups (—$CX_2$—CXY—) of the substances (S2) of the family (F'1).

A second family of preferred substances corresponding to the formula (II) is that where Y represents a phenyl group, optionally substituted with one or more atoms chosen from halogen atoms other than the iodine atom and $C_1$-$C_8$ alkyl groups [family (F'''2)].

The groups (—$CX_2$—CXY—) of the substances of the family (F'''2) satisfy the same characteristics and conditions preferably as the groups (—$CX_2$—CXY—) of the substances (S2) of the family (F'2).

A third family of preferred substances corresponding to the formula (II) is that where Y represents a group, —O—C(=O)—Z, Z as defined above [family (F'''3)].

The groups (—$CX_2$—CXY—) of the substances of the family (F'''3) satisfy the same characteristics and conditions preferably as the groups (—$CX_2$—CXY—) of the substances (S2) of the family (F'3).

A fourth family of preferred substances corresponding to the formula (II) is that where Y represents a group chosen from the nitrile groups, —C(=O)—O—Z and —C(=O)—NZ$_2$, Z as defined above [family (F'''4)].

The groups (—CX$_2$—CXY—) of the substances of the family (F'''4) satisfy the same characteristics and conditions preferably as the groups (—CX$_2$—CXY—) of the substances (S2) of the family (F'4).

The invention also relates to an iodinated organic substance having a molecular mass of less than 2000, corresponding to the general formula R—O—S(=O)$_p$—O(—CX$_2$—CXY—)I    (III)

with R, X, Y, I and p as defined above for the substances (S2).

The substance corresponding to the formula (III) has a molecular mass preferably of less than 1000, in a particularly preferred manner of less than 500 and in a most particularly preferred manner of less than 250.

As regards the substance corresponding to the formula (III), p is preferably equal to 2.

A first family of preferred substances corresponding to the formula (III) is that where Y represents a halogen atom other than an iodine atom (family [F$^{IV}$1]).

The groups (—CX$_2$—CXY—) of the substances of the family (F$^{IV}$1) satisfy the same characteristics and conditions preferably as the groups (—CX$_2$—CXY—) of the substances (S2) of the family (F'1).

A second family of preferred substances corresponding to the formula is that where Y represents a phenyl group, preferably substituted with one or more atoms chosen from halogen atoms other than the iodine atom and C$_1$-C$_8$ alkyl groups [family (F$_{IV}$2)].

The groups (—CX$_2$—CXY—) of the substances of the family (F$^{IV}$2) satisfy the same characteristics and conditions preferably as the groups (—CX$_2$—CXY—) of the substances (S2) of the family (F'2).

A third family of preferred substances corresponding to the formula (III) is that where Y represents a group —O—C(=O)—Z, Z as defined above [family (F$_{IV}$3)].

The groups (—CX$_2$—CXY—) of the substances of the family (F$_{IV}$3) satisfy the same characteristics and conditions preferably as the groups (—CX$_2$—CXY—) of the substances (S2) of the family (F'3).

A fourth family of preferred substances corresponding to the formula (III) is that where Y represents a group chosen from the nitrile group, the groups —C(=O)=O—Z and —C(=O)—NZ$_2$, Z as defined above [family (F$^{IV}$4)].

The groups (—CX$_2$—CXY—) of the substances of the family (F$_{IV}$4) satisfy the same characteristics and conditions preferably as the groups (—CX$_2$—CXY—) of the substances (S2) of the family (F'4).

The subject of the present invention is finally a process of controlled free-radical polymerization using the iodinated organic substances according to the invention or prepared by the process of synthesis according to the invention and which has all the advantages of the controlled free-radical polymerization processes of the prior art without exhibiting the disadvantages thereof.

To this effect, the invention relates to a process for preparing a polymer by free-radical polymerization of at least one ethylenically unsaturated monomer, using in the polymerization:

(A') the ethylenically unsaturated monomer,
(B') at least one free-radical-generating agent chosen from peroxides, diazo compounds, dialkyldiphenylalkanes, substances derived from tetraphenylethane, boranes, iniferter substances comprising at least one thiuram disulphide group, styrene and styrene substances, and ultraviolet radiation,
(C') one or more substances chosen from the substances (S) prepared by the process for preparing iodinated organic substances as described above, the iodinated organic substances (S2) of the mixtures as described above and the iodinated organic substances as described above, and, optionally in addition,
(D') at least one complex of a metal chosen from transition metals, lanthanides, actinides and group ma metals, and of a ligand of this metal.

By way of examples of ethylenically unsaturated monomers, there may be mentioned vinyl esters as vinyl acetate, acrylic acid, acrylic esters such as methyl acrylate, methacrylic acid, methacrylic esters such as methyl methacrylate, nitriles and acrylic or methacrylic amides, styrene monomers such as styrene, olefin monomers such as butadiene and halogenated vinyl monomers.

The expression "halogenated vinyl monomers" is understood to mean an ethylenically unsaturated monomer comprising one or more halogen atoms, and not comprising a heteroatom other than this or these halogen atoms.

By way of examples of halogenated vinyl monomers, there may be mentioned vinyl chloride, vinylidene chloride, trichloroethylene, chloroprene and chlorotrifluoroethylene, vinyl fluoride, vinylidene fluoride, trifluoroethylene, tetrafluoroethylene, hexafluoropropylene and chlorotrifluoroethylene.

(A') preferably comprises at least one halogenated vinyl monomer. In a particularly preferred manner, (A') is composed of a halogenated vinyl monomer and, optionally in addition, of an acrylic ester.

The process of polymerization according to the invention advantageously comprises the steps according to which:

(1') at least a fraction of (A'), at least a fraction of (B'), at least a fraction of (C') and, where appropriate, at least a fraction of (D') are introduced into a reactor,
(2') the contents of the reactor are caused to react, while introducing therein the possible remainder of (A'), the possible remainder of (B'), the possible remainder of (C') and, where appropriate, the possible remainder of (D'), until a moment is reached when the contents of the reactor comprise the polymer.

Preferably, the process of polymerization according to the invention comprises the steps according to which:

(1") at least a fraction of (A'), at least a fraction of (B'), and, where appropriate, at least a fraction of (D') are introduced into a reactor, the said reactor containing one or more substances (C') prepared beforehand by the process for preparing iodinated organic substances as described above,
(2") the contents of the reactor are caused to react, while introducing therein the possible remainder of (A'), the possible remainder of (B'), the possible remainder of (C') and, where appropriate, the possible remainder of (D'), until a moment is reached when the contents of the reactor comprise the polymer.

According to a first preferred variant of the process of polymerization according to the invention, the latter does not use in the polymerization a complex of a metal chosen from transition metals, lanthanides, actinides and group ma metals, and of a ligand of this metal.

According to a second preferred variant of the process of polymerization according to the invention, the latter uses in the polymerization at least one complex of a metal chosen from transition metals, lanthanides, actinides and group ma metals, and of a ligand of this metal.

The process for preparing iodinated organic substances according to the invention has multiple advantages. It is very easy to carry out. It uses raw materials which are inexpensive and not very dangerous to handle. The iodinated organic substances thus produced are themselves inexpensive.

It allows in situ synthesis, in a polymerization reactor, prior to carrying out a controlled free-radical polymerization of the ITP type (without a metal-ligand complex) or ATRP type (Atom Transfer Radical Polymerisation, in the presence of metal-ligand complexes), of initiators of the said polymerization. Such initiators can therefore be synthesized without having available appropriate synthesis reactors or storage reservoirs for the raw materials necessary for these syntheses. What is more, these initiators may be custom made, so as to be particularly well suited to the controlled free-radical polymerization in which they will be used.

EXAMPLE 1

1.627 g ($1.56 \times 10^{-2}$ moles) of styrene, 0.0292 g ($1.15 \times 10^{-4}$ moles) of molecular iodine, 0.0286 g ($1.95 \times 10^{-4}$ moles) of di-tert-butyl peroxide and 1.684 g of benzene were introduced into a 10 ml Carius tube. Argon was bubbled through so as to remove oxygen therefrom, and then the tube was frozen in liquid nitrogen and sealed under vacuum.

Next, the tube was placed in an oven heated to 120° C., and its contents, initially dark brown in colour, were allowed to react therein until their complete decolorization was obtained, which decolorization occurred 15 hours after the tube was placed in the oven.

At this moment, the tube was removed from the oven and its contents were cooled to room temperature.

The products of the reaction were separated and their chemical nature determined by size exclusion chromatography applied to the crude contents of the reactor.

To this effect, a plant was used composed of a Waters Associates pump equipped with a refractometric detector Shodex RIse-61 and two mixed-C PL-gel 5 μm columns from the company Polymer Laboratories. The plant was standardized by means of a polystyrene standard. Tetrahydrofuran was used as eluent, at a flow rate of 1.0 ml/min.

Figure 1:
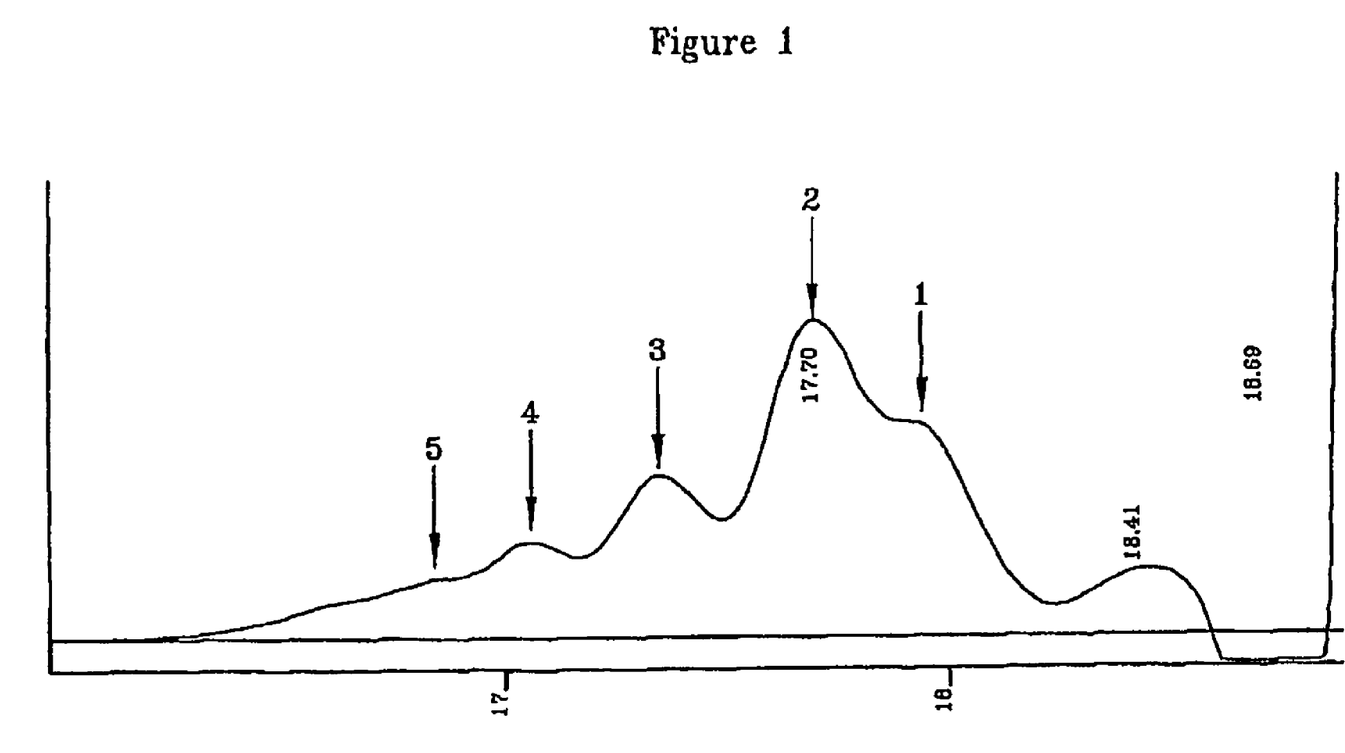
FIG. 1 shows the chromatogram of the products of Example 1.

The following results, illustrated by the chromatogram in FIG. 1, were obtained:

the reaction produced iodinated organic substances having a number-average molecular mass of 299, very close to that of the compound corresponding to the formula (CH3)3C—O(CH2—CHΦ)I;

size exclusion chromatography made it possible to separate and identify five (pairs of) iodinated organic substances corresponding to the formula A (—CH$_2$—CHΦ-)$_n$—I, where Φ denotes a phenyl group, n is equal to 0 to 4 and A denotes a tert-butoxy (CH$_3$)$_3$C—O— and/or methyl group, the said methyl group being itself reputed to result from the β-cleavage of the tert-butoxy group;

the following correspondences were made: the peak 1 (molecular mass in the region of 239) was associated with n=0; the peak 2 (molecular mass in the region of 277) was associated with n=1; the peak 3 (molecular mass in the region of 367) was associated with n=2; the peak 4 (molecular mass in the region of 460) was associated with n=3; the peak 5 (molecular mass in the region of 558) was associated with n=4.

EXAMPLE 2

25 ml of 1,2-dichloroethane, 10 g (0.1163 mole) of vinyl acetate, 0.8 g (0.0031 mole) of molecular iodine and 1.0 g (0.0056 mole) of diethyl peroxydicarbonate were introduced into a 250 ml two-necked round-bottomed flask surmounted by a condenser and immersed in an oil bath. The contents of the round-bottomed flask had a dark colour. The contents of the round-bottomed flask were deaerated by bubbling nitrogen through for 30 min. Next, the contents of the round-bottomed flask were heated to 65° C. and they were allowed to react until complete decolorization was obtained, which decolorization was obtained 73 minutes later. The contents of the two-necked round-bottomed flask were rapidly cooled. It contains iodinated organic substances according to the invention.

EXAMPLE 3

25 ml of 1,2-dichloroethane, 10 g (0.1163 mole) of vinyl acetate, 1.5 g (0.0059 mole) of molecular iodine and 1.0 g (0.0056 mole) of diethyl peroxydicarbonate were introduced into a 250 ml two-necked round-bottomed flask surmounted by a condenser and immersed in an oil bath. The contents of the round-bottomed flask had a dark colour. The contents of the round-bottomed flask were deaerated by bubbling nitrogen through for 30 min. Next, the contents of the round-bottomed flask were heated to 65° C. and they were caused to react The temperature of 65° C. was maintained for a sufficiently long period, that is 5 hours, such that the quantity of vinyl acetate consumed by the reaction no longer changes. After reaction, it was observed that the contents of the round-bottomed flask has retained a dark colour. It contains iodinated organic substances according to the invention.

EXAMPLE 4

25 ml of 1,2-dichloroethane, 14.85 g (0.116 mole) of n-butyl acrylate, 0.8 g (0.0031 mole) of molecular iodine and 1.0 g (0.0056 mole) of diethyl peroxydicarbonate were introduced into a 250 ml two-necked round-bottomed flask surmounted by a condenser and immersed in an oil bath. The contents of the round-bottomed flask had a dark colour. The contents of the round-bottomed flask were deaerated by bubbling nitrogen through for 30 min. Next, the contents of the round-bottomed flask were heated to 65° C. and they were allowed to react until complete decolorization was obtained, which decolorization was obtained 98 minutes later. The contents of the two-necked round-bottomed flask were rapidly cooled. It contains iodinated organic substances according to the invention.

EXAMPLE 5

25 ml of 1,2-dichloroethane, 14.85 g (0.116 mole) of n-butyl acrylate, 1.4 g (0.0055 mole) of molecular iodine and 0.85 g (0.0052 mole) of azobis(isobutyronitrile) were introduced into a 250 ml two-necked round-bottomed flask surmounted by a condenser and immersed in an oil bath. The contents of the round-bottomed flask had a dark colour. The latter was heated to 65° C. and they were caused to react. The temperature of 65° C. was maintained for a sufficiently long period, that is 5 hours, such that the quantity of n-butyl acrylate consumed by the reaction no longer changes. After reaction, it was observed that the contents of the round-bottomed flask had retained a dark colour. It contains iodinated organic substances according to the invention.

The invention claimed is:

1. A process for preparing one or more iodinated organic substances having a molecular mass of less than 2000 (substances (S)) using:
   (A) at least one free-radical-generating substance chosen from peroxides, diazo compounds, dialkyldiphenylalkanes, substances derived from tetraphenylethane, boranes and iniferter substances comprising at least one thiuram disulphide group,
   (B) at least one organic substance comprising at least one ethylenic double bond, capable of adding a free radical to its ethylenic double bond,
   (C) molecular iodine,
   which comprises:
   (1) introducing at least a fraction of (A), at least a fraction of (B) and at least a fraction of (C) into a reactor, then
   (2) causing the contents of the reactor to react, while introducing therein the possible remainder of (A), the possible remainder of (B) and the possible remainder of (C), until the reactor comprises a mixture comprising one or more substances (S) [mixture (M)], and then
   either the contents of the reactor are caused to react until the quantity of (B) consumed by the reaction no longer changes (variant (1)), or the reaction in progress is stopped (variant (2)), to produce said one or more iodinated organic substances having a molecular mass of less than 2000,
   wherein in variant (1), the number of moles of (C) introduced into the reactor expressed relative to the number of moles of (A) introduced into the reactor is greater than or equal to 90% and less than 200% and the number of moles of (C) introduced into the reactor expressed relative to the number of moles of (B) introduced into the reactor is more than 0.5% and less than 200%,
   wherein in variant (2) the number of moles of (C) introduced into the reactor expressed relative to the number of moles of (A) introduced into the reactor is greater than or equal to 20% and less than 100% and the number of moles of (C) introduced into the reactor expressed relative to the number of moles (B) introduced into the reactor is greater than or equal to 0.01% and less than 5%, and
   wherein the at least one organic substance comprising at least one ethylenic double bond, capable of adding a free radical to its ethylenic double bond, is at least one compound corresponding to the formula:

where
   the Ψ symbols represent, independently of each other and of Ξ, (i) a hydrogen atom, (ii) a halogen atom other than iodine, or (iii) a linear or branched C1-C20 alkyl group;
   Ξ represents (i) a halogen atom other than iodine, (ii) a phenyl group optionally substituted with one or more atoms chosen from halogen atoms other than iodine and $C_1$-$C_8$ alkyl groups, (iii) —O—C(=O)-Ω, (iv) a nitrile group, (v) —C(=O)—O-Ω or (vi) —C(=O)—N-Ω; and
   Ω represents (i) a hydrogen atom, or (ii) a saturated or ethylenically unsaturated or aromatic $C_1$-$C_{20}$ hydrocarbon group.

2. The process according to claim 1, wherein the substance(s) (S) have a molecular mass of less than 1000.

3. The process according to claim 1, wherein the substance(s) (S) have a number-average molecular mass of less than 500.

4. The process according to claim 1, comprising variant (2), wherein the reaction in progress is stopped when the color of the contents of the reactor changes from a dark color to a light color.

5. The process according to claim 1, comprising variant (1).

6. The process according to claim 5, wherein the number of moles of (C) introduced into the reactor expressed relative to the number of moles of (A) introduced into the reactor is greater than or equal to 100% and less than 150% and the number of moles of (C) introduced into the reactor expressed relative to the number of moles of (B) introduced into the reactor is more than 0.5% and less than 150%.

7. The process according to claim 1, comprising variant (2).

8. The process according to claim 7, wherein the reaction in progress is stopped by cooling the contents of the reactor.

9. The process according to claim 7, wherein the number of moles of (C) introduced into the reactor expressed relative to the number of moles of (A) introduced into the reactor is greater than or equal to 20% and less than 90% and the number of moles of (C) introduced into the reactor expressed relative to the number of moles (B) introduced into the reactor is greater than or equal to 0.1% and less than 5%.

10. The process according to claim 5, further comprising isolating at least one substance (S) from the mixture (M) after the contents of the reactor are caused to react until the quantity of (B) consumed by the reaction no longer changes.

11. The process according to claim 7, further comprising isolating at least one substance (S) from the mixture (M) after the reaction in progress is stopped.

12. The process according to claim 1, wherein all of each of (A), (B) and (C) are introduced into the reactor in (1).

13. A process for preparing one or more iodinated organic substances having a molecular mass of less than 2000 (substances (S)) using:
   (A) at least one free-radical-generating substance chosen from peroxides, diazo compounds, dialkyldiphenylalkanes, substances derived from tetraphenylethane, boranes and iniferter substances comprising at least one thiuram disulphide group,
   (B) at least one organic substance comprising at least one ethylenic double bond, capable of adding a free radical to its ethylenic double bond,
   (C) molecular iodine,
   which comprises:
   (1) introducing at least a fraction of (A), at least a fraction of (B) and at least a fraction of (C) into a reactor, then
   (2) causing the contents of the reactor to react, while introducing therein the possible remainder of (A), the possible remainder of (B) and the possible remainder of (C), until the reactor comprises a mixture comprising one or more substances (S) [mixture (M)], and then
   either the contents of the reactor are caused to react until the quantity of (B) consumed by the reaction no longer changes (variant (1)), or the reaction in progress is stopped (variant (2)), to produce said one or more iodinated organic substances having a molecular mass of less than 2000,
   wherein in variant (1), the number of moles of (C) introduced into the reactor expressed relative to the number of moles of (A) introduced into the reactor is greater than or equal to 90% and less than 200% and the number of moles of (C) introduced into the reactor expressed relative to the number of moles of (B) introduced into the reactor is more than 0.5% and less than 200%.
   wherein in variant (2) the number of moles of (C) introduced into the reactor expressed relative to the number of moles of (A) introduced into the reactor is greater than or equal to 20% and less than 100% and the number of moles of (C) introduced into the reactor expressed relative to the number of moles (B) introduced into the reactor is greater than or equal to 0.01% and less than 5%, and wherein the at least one organic substance comprising at least one ethylenic double bond, capable of adding a free radical to its ethylenic double bond, is at least one of vinyl chloride, vinylidene chloride, trichloroethylene, chlorotrifluoroethylene, vinyl fluoride, vinylidene fluoride, trifluoroethylene, tetrafluoroethylene, hexafluoropropylene, styrene, vinyl acetate, acrylic acid, methyl acrylate, ethyl acrylate, n-butyl acrylate, 2-ethylhexyl acrylate, methacrylic acid, methyl methacrylate, n-butyl methacrylate, ethylene, propylene and butadiene.

14. The process according to claim 13, wherein the substance(s) (S) have a molecular mass of less than 1000.

15. The process according to claim 13, wherein the substance(s) (S) have a number-average molecular mass of less than 500.

16. The process according to claim 13, comprising variant (2), wherein the reaction in progress is stopped when the color of the contents of the reactor changes from a dark color to a light color.

17. The process according to claim 13, comprising variant (1).

18. The process according to claim 13, comprising variant (2).

19. The process according to claim 13, wherein all of each of (A), (B) and (C) are introduced into the reactor in (1).

* * * * *